United States Patent
Breidler et al.

(10) Patent No.: US 10,145,771 B2
(45) Date of Patent: Dec. 4, 2018

(54) METHOD, DEVICE AND COMPUTER MEDIUM FOR DETERMINING THE DENSITY OF LIQUIDS

(71) Applicant: ANTON PAAR GMBH, Graz-Strassgang (AT)

(72) Inventors: Robert Breidler, Graz (AT); Gerald Steiner, Graz (AT); Rupert Gruellenberger, Graz (AT)

(73) Assignee: Anton Paar GmbH, Graz-Strassgang (AT)

(*) Notice: Subject to any disclaimer, the term of this patent is extended or adjusted under 35 U.S.C. 154(b) by 153 days.

(21) Appl. No.: 15/223,222

(22) Filed: Jul. 29, 2016

(65) Prior Publication Data

US 2017/0030816 A1 Feb. 2, 2017

(30) Foreign Application Priority Data

Jul. 29, 2015 (AT) .............................. A 50680/2015

(51) Int. Cl.
*G01N 9/00* (2006.01)

(52) U.S. Cl.
CPC ....... *G01N 9/002* (2013.01); *G01N 2009/006* (2013.01)

(58) Field of Classification Search
CPC ............. G01N 9/00; G01N 9/002; G01N 9/36
USPC ................................................ 73/32 R, 32 A
See application file for complete search history.

(56) References Cited

U.S. PATENT DOCUMENTS

| 2005/0035867 A1* | 2/2005 | Matt ...................... G01D 1/18 340/601 |
| 2011/0000321 A1* | 1/2011 | Forrer .................... G01N 9/002 73/863.71 |

* cited by examiner

*Primary Examiner* — Benjamin Schmitt
(74) *Attorney, Agent, or Firm* — Laurence A. Greenberg; Werner H. Stemer; Ralph E. Locher

(57) ABSTRACT

A method and a measuring device determine the density of liquids. The measuring device has a flexural resonator, at least one sensor for at least one environmental parameter that influences a measurement to be performed and a condition monitoring unit. The measured values from the respective sensor are fed to the condition monitoring unit. The condition monitoring unit has a memory unit with stored forecasts for environmental parameters to be expected in the course of the measurement, and that, by using the condition monitoring unit, on the basis of the stored forecasts and the initial measured values selected for the measurement, it is determined whether the planned measurement can be carried out under the selected trial conditions without any impairment or with a permissible impairment by the forecast changes in the environmental parameters.

12 Claims, 1 Drawing Sheet

METHOD, DEVICE AND COMPUTER MEDIUM FOR DETERMINING THE DENSITY OF LIQUIDS

CROSS-REFERENCE TO RELATED APPLICATION

This application claims the priority, under 35 U.S.C. § 119, of Austrian application AT A50680/2015, filed Jul. 29, 2015; the prior application is herewith incorporated by reference in its entirety.

BACKGROUND OF THE INVENTION

Field of the Invention

The invention relates to a method, a measuring device and a data carrier for determining the density of a fluid.

For the accurate determination of the density of a fluid with a flexural resonator, stable environmental conditions and a defined operating state of the flexural resonator are necessary. Otherwise, the measurement can be influenced detrimentally by disruptive environmental influences, such as air pressure, atmospheric humidity, temperature, dust particles, chemical vapors, shocks and/or vibrations, as far as damage to or destruction of the flexural resonator in the event of long-term presence of the disruptive influence.

In particular for the highly accurate determination of the density of liquids, a stable temperature of the measuring cell is vital. In many applications, the measuring temperature lies below the ambient temperature. Typical measuring temperatures are 15° C., 20° C., 60° C. For special applications, the temperature also often lies below 10° C. In particular, the operation of a measuring cell in a moist, warm environment constitutes a challenge, since the operating state can lead to the formation of condensation in the measuring cell, which can lead to destruction of the latter.

In the event of many measuring errors and of damage to devices in the field, the causes and if need be the question of liability cannot be clarified, since the triggering and actual conditions cannot be reconstructed.

It is known to encapsulate measuring cells in a dust-tight and gas-tight manner for process applications and therefore to minimize the influence of the environmental conditions. It is also known to equip the housing of measuring cells with flexural resonators with dry air purging or to integrate drying cartridges into the housing. Measuring cells constructed to be gas-tight are expensive and can be implemented technically only with very great difficulty; most of the time only specific influences can be ruled out with such solutions. For instance, dry air purging or the use of drying cartridges is operationally reliable only to a limited extent, primarily with regard to the errors by the user. If the dry air purging is not connected correctly, condensation can form in the housing interior, which can lead to destruction of the measuring cell.

SUMMARY OF THE INVENTION

The aim of the invention is the avoidance of the disadvantages of known measuring devices and methods and the creation of a measuring device and measuring method that can be used optionally under different environmental conditions.

According to the invention, for a method of the type mentioned at the beginning, it is proposed that the measuring device has at least one sensor for at least one environmental parameter of the flexural resonator and/or the measuring device that influences a measurement, in particular a series of measurements, to be performed, preferably atmospheric humidity and/or air pressure and/or air temperature, and has a condition monitoring unit. The measured values from the respective sensor are fed to the condition monitoring unit, and the condition monitoring unit has a memory unit with stored forecasts and prediction algorithms for environmental parameters to be expected in the course of the measurement and for operating states to be expected. By using the condition monitoring unit, on the basis of the stored forecasts and algorithms and depending on the present and/or expected values of the environmental parameters and the initial measured values or conditions selected for the measurement, it is determined whether the planned measurement, in particular series of measurements, can be carried out under the selected trial conditions and/or the initial values present at the start of measurement and/or with the parameter values selected or expected in the course of the measurement, without any impairment or with a permissible impairment by the expected or forecast changes in the environmental parameters.

According to the invention for a device of the type mentioned at the beginning, it is proposed that the measuring device has at least one sensor for at least one environmental parameter of the flexural resonator and/or the measuring device that influences a measurement, in particular a series of measurements, to be performed, preferably atmospheric humidity and/or air pressure and/or air temperature, and has a condition monitoring unit, to which the measured values from the respective sensor are fed. The condition monitoring unit has a memory unit with stored forecasts and prediction algorithms for the determination of values of the environmental parameters to be expected in the course of the measurement. On the basis of the stored forecasts and algorithms and depending on the present and/or predefined values of the environmental parameters and the initial values of the environmental parameters selected for the measurement, it is determined whether the planned measurement in particular series of measurements, can be carried out under the selected trial conditions and/or with the selected initial values and/or with the parameter values selected or expected in the course of the measurement without any impairment or with a permissible impairment by the expected or forecast changes in the environmental parameters.

The condition monitoring unit and the sensors connected to the latter, where appropriate, measure and store all the relevant environmental parameters which can have an influence on the measured result and/or on the service life of the flexural resonator. Furthermore, it creates forecasts relating to the future values and/or changes in the parameters by use of the prediction algorithms. The parameters recorded can be, for example, air pressure, atmospheric humidity, temperature, dust particles, chemical vapors, shocks and/or vibrations. Finally, the condition monitoring unit also controls actuators for setting the parameters in the close environment of the measuring cell or in the measuring cell. This primarily involves regions up to about 100 cm around the measuring cell or the flexural resonator, but preferably around regions in the housing of the measuring device, since the atmosphere in the housing is significant for the operation of the resonator and, for example, the inherent heating of the system by the measurement conditions can be taken into account. If appropriate, a combination of sensors outside and inside the housing can also be used.

Via a user interface, the user is informed about the current and forecast operating state of the measuring device, depending on the environmental parameters for example an expected fall below the dew point in the event of setting an excessively low measuring cell temperature. In addition, before the start of a measurement, it can be estimated by the condition monitoring unit whether the measurement can be carried out in particular with different operating parameters of the flexural resonator, under the environmental conditions to be expected and/or which are prevailing, without additional measures and within a valid operating state without undesired influences. Such a preventive function prevents the user from wasting unnecessary time for measurements which cannot be carried out correctly.

The invention further offers the possibility of being able to reconstruct more easily the course of failures and measurement errors by the storage of the operating states and environmental variables and parameters occurring during use of the device.

By means of the invention the construction of measuring cells which contain sensitive sensors can be configured more economically and simplified; for example encapsulation of the flexural resonator is no longer required, since the correct operating state s monitored by the condition monitoring unit and predicted or ensured for the future.

It is advantageous if the measuring device has at least one actuator for setting or controlling at least one environmental parameter, with which actuator, before and/or during the measurement, at least one environmental parameter is controlled or set, preferably by the condition monitoring unit, on the basis of correction values which are determined by the condition monitoring unit or predefined.

Via the actuators activated by the condition monitoring unit for regulating the environmental conditions outside or around the cell and/or within the measuring cell, suitable measures can automatically be taken in order to ensure the valid or desired operating state for a complete measurement, e.g. automatic dry air purging during low-temperature trials which, without dry air purging, could lead to condensation in the measuring cell and could distort the measured results or lead to destruction of the flexural resonator, or activation of a particle filter or regeneration of a drying cartridge and/or a particle filter, or a reduction in the air volume in the interior of the measuring cell of the device, or active vibration compensation or mechanical encapsulation. The requisite components and actuators for eliminating disruptive environmental conditions and influences can also be installed in the measuring device itself, for example in the form of an integrated membrane dryer and activation of an internal air pump.

It is advantageous, as environmental parameters, to monitor or to determine the air pressure, the air temperature and/or the relative atmospheric humidity in the near environment of the measuring chamber, for example in the radius of one meter or in the housing of the measuring device, and, for example, to determine the dew point temperature from the aforementioned parameters. The relationship of these parameters is known and can be derived from the Magnus formula for describing the saturation vapor pressure. If the measuring cell temperature falls below the dew point temperature, the sensor can react automatically thereto and inform the user and the condition monitoring unit that the dew point has been undershot. The condition monitoring unit increases the measuring cell temperature independently or via an entry by the user in order to prevent the measuring cell misting up. In the case of purging with dry air, the sensor is used to monitor the dry air purging. If the latter is switched off or fails, this can be detected by the sensors, and the user is warned or the measuring device is brought into a safe operating state, since the atmospheric humidity sensor functions only as long as the water vapor is not deposited as dew.

For this case, a dew point sensor can additionally be placed at a suitable location, i.e. the coldest location, directly in the measuring cell. This can be implemented, for example, by a capacitive sensor. One important possibility is the analysis of the time profile of the state parameters for the extrapolation or prediction of the profile of the dew point temperature for the early detection of undershooting the dew point.

The invention offers the advantageous possibility of an analysis of the time profile of the state parameters for the extrapolation of the profile of the interference variable for the early detection of the problematic operating state even before the latter is reached.

Also significant is the possibility of storing the operating states occurring during use of the device and the changing environmental parameters, in order to be able to reconstruct the course of failures more easily.

The disturbances from the environment penetrating into the housing or into the measuring cell can cause many problems, specifically in the case of flexural resonators; e.g. deposition of dust and precipitation of humidity on the flexural resonator has the effect that the flexural resonator changes frequency, which means the optical detection of bubbles is made more difficult. Vibrations can interfere with the measured values for the natural frequency or cause erroneous measurements in the averaging as a result of outliers. Highly deviating environmental temperatures can lead to drift in a temperature-controlled flexural resonator. According to the invention, these influences can be eliminated.

Other features which are considered as characteristic for the invention are set forth in the appended claims.

Although the invention is illustrated and described herein as embodied in a method for determining the density of liquids, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
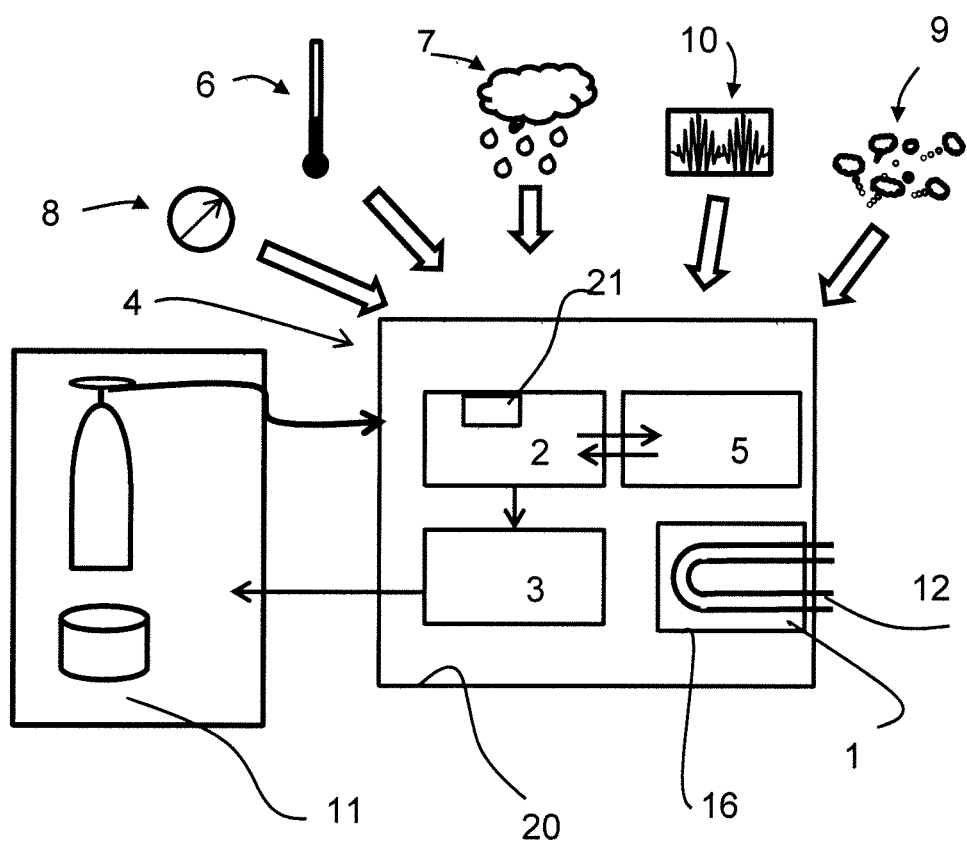
FIG. 1 is an illustration showing in schematic form a structure of a measuring device according to the invention.

Referring now to the figures of the drawings in detail and first, particularly to FIG. 1 thereof, there is shown a measuring device 4 according to the invention, in the present case a measuring device for determining the density of liquids. The measuring device 4 contains a flexural resonator 12, which is arranged within an advantageously open housing 20 and together with this housing 20 forms a measuring cell 1. The liquid to be examined is fed to and discharged from the flexural resonator 12 at its ends, as known per se, and the measured values from the oscillation are tapped off and evaluated. The units required for this purpose are known and not illustrated. As illustrated schematically in FIG. 1, the measuring device 4 contains the measuring cell 1, which accommodates the flexural resonator 12 in its housing 20, and a corresponding sample feed 22. Furthermore, the measuring device 4 contains a condition monitoring unit 2 with a memory unit 21, in which stored forecasts and prediction algorithms for changes in environmental parameters to be expected in the course of the measurement are contained. Actuators 3 are connected to the condition monitoring unit 2. Such an actuator 3 is provided, for example, for actuating a feed device 11 for fresh air or a filter unit. Furthermore, a number of sensors responding to different environmental parameters are connected to the condition monitoring unit 2. In particular, this can be a sensor 6 for temperature measurement and/or a sensor 7 for humidity measurement of the air surrounding the measuring device 4 or the air located in the measuring cell 1. Furthermore, a sensor 8 for determining the air pressure, a sensor 9 for determining the dust content of the air surrounding the measuring device 4 or the dust located in the measuring cell 1 may be present. A sensor 10 for determining shocks and/or vibrations acting on the measuring device 4 can also be provided. These sensors 6, 7, 8, 9, 10 output their measured values to the condition monitoring unit 2 which, by using the stored forecasts and algorithms, create the measuring conditions for a planned measurement. If the condition monitoring unit 2 arrives at the result that the measurement can be performed uninfluenced by these environmental or ambient parameters, then the output of a warning signal is suppressed and the measurement is permitted. If the condition monitoring unit determines that a predefined limiting value has been exceeded by at least one measured value of an environmental parameter at the time of determination of the parameter values or for the future, then a warning signal is output and the performance of the measurement is prevented.

Figure 2:
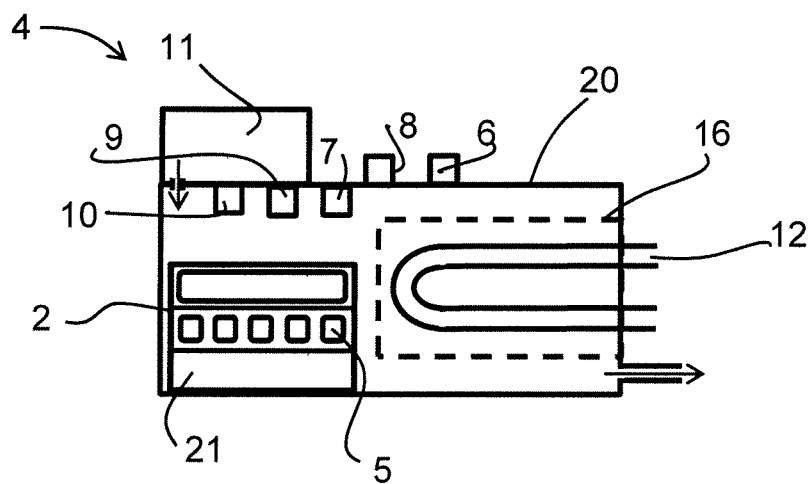
FIG. 2 is a sectional view of the measuring device according to the invention.

Illustrated in FIG. 2 is the measuring device 4 which, with its housing 20, accommodates the flexural resonator 12 with an encapsulation 16 of the latter. The actuator provided is a unit 11 for the supply of inert gas and/or dry air, which can be controlled on the basis of the control from the condition monitoring unit 2. Reference numeral 5 designates an input-output unit or a user interface for the condition monitoring unit 2, with which appropriate commands can be transmitted to the condition monitoring unit 2 and into which a data carrier for programs to be executed by the condition monitoring unit 2, if need be with stored forecasts and prediction algorithms, can be input.

The condition monitoring unit 2 can communicate with the user via the user interface 5. Via the user interface 5, appropriate commands are input and measured values and data are read out.

The invention is primarily based on the idea of equipping a measuring device 4 with additional sensors 6, 7, 8, 9, 10 in the housing 20 or on the housing 20, the sensors checking the operating state of the measuring device 4 for safe conditions meeting a standard in the interior of the housing 20 of the flexural resonator 12 and/or in the environment of an open housing 20 of the measuring device 4 and/or flexural resonator 12.

It is advantageous if, when specific temperature values are reached or as early as when a selected temperature is predefined, the relative atmospheric humidity is pre-determined on the basis of the atmospheric or environmental parameters in the interior of the device or interior of the housing 20 of the flexural resonator 12, and therefore the conditions occurring are predicted even before the start of cooling. It is also advantageous to perform monitoring and prior calculation of the dew point on the basis of the desired temperature profile and the environmental parameters.

It is possible to output a warning to the user when the selected trial parameters are not safe.

Furthermore, a definition of limiting values for specific accuracy classes can be predefined and/or it can be suggested to the user that specific values of environmental parameters can be achieved or not achieved by the use of specific precautions or actuators, for example by purging with dry air, by adapting the climatic conditions in the room around the measuring device, by lowering the temperature and/or dehumidifying, by starting up an air conditioning system and/or by lowering the temperature in the room via the air conditioning system, all in the surrounding area of the measuring device.

The prediction of a valid operating state for the flexural resonator 12 and the assessment of the selected trial conditions are important. In the event of cooling below room temperature, for example, the dew point can be pre-calculated and, from the data for the surrounding area, the permissibility of cooling within certain limits can be checked.

Thus, sensors 6, 7, 8, 9, 10 are provided, with which at least one environmental parameter, e.g. humidity, temperature, dust and/or vibrations, is measured. For the dew point determination, for example, sensors for the temperature and the atmospheric humidity and possibly the air pressure are required.

The flexural resonator 12 can, for example, be equipped with an additional temperature control unit, a sensor 6 connected to the condition monitoring unit 2 measuring the temperature of the sample or of the flexural resonator 12. A further possible way of monitoring the measurement is, for example, monitoring the sample pressure, e.g. when filling the flexural resonator 12.

According to the invention, it becomes possible to leave out the encapsulation 16 of the flexural resonator 12, above all for process applications; it is then possible above all to operate the flexural resonator 12 without any sheathing either if the air in the housing 20 is kept dry enough.

For accurate measuring devices but also for process devices encapsulated in a fluid-tight manner, for example, specific device conditions must be met. These are normally specified in the description or operating instructions for the respective accuracy class of the flexural resonator. Deviations from these conditions are not always detectable by the user. According to the invention, the environmental conditions are controlled and/or predefined; therefore compliance with the device conditions can also be checked by using the sensors proposed.

During the input of trial sequences, prior calculation of the applicable trial conditions on the basis of the previously measured environmental parameter values is possible. For example, a temperature control system and/or temperature control unit of the resonator can if necessary prevent the latter from undesired cooling.

During the input of the temperature profile, for example, the dew point can be estimated from the Magnus formula.

The maximum possible water vapor pressure at a specific temperature is designated as the saturation vapor pressure. For the calculation of the saturation vapor pressure over water and ice, there is in the literature a large number of approximation formulas for the individual temperature ranges; one of these is the Magnus formula, which is approximately true over water for a temperature range from −50 to +100° C. The saturation vapor pressure $e_{sat,W}$ of water vapor in Pascal (for the standard air pressure of 101325 Pa) results from the temperature T in ° C.

$$e_{sat,W} = 611.12 * \exp\frac{17.62 * T}{(243.12 + T)}$$

calculated from an approximation formula via the dew point temperature, which designates that temperature at which the water vapor saturation concentration or the water vapor saturation pressure of the air is reached.

The relative atmospheric humidity in this state is φ=1. If the moist air cools down below the dew point temperature, a phase change from gaseous to liquid occurs and part of the water vapor contained in the air is separated out as excess moisture in liquid form as dew, where it is true that:

$$t_t = \varphi^{\frac{1}{8.02}} * (109.8 + t) - 109.8$$

(with φ . . . relative atmospheric humidity, T . . . temperature in ° C.).

Depending on the desired accuracy class and the sensors available, other approximation solutions can also be stored, if necessary whilst taking account of the air pressure in the condition monitoring unit 2 functioning as evaluation unit. For other environmental parameters, other algorithms apply.

In many operating cases, the complicated continuous purging with dry air is not necessary, since the operating conditions with regard to temperature and external atmospheric humidity are sufficient to permit condensation-free operation of the measuring device 4. Under extreme weather conditions and extreme measuring conditions, e.g. low temperatures, switching on drying air is absolutely necessary—either the user can be requested via the user interface 5 to do this, or else that is done automatically via an actuator and/or control element 11 or the condition monitoring unit 2.

For all measuring devices with flexural resonators 12 in non-tight or open housings 20, the invention can be implemented relatively simply and economically.

In many cases, users can operate the measuring device without danger or be made aware of measurements which lie outside the standard conditions—specifically before they come to lie outside the standard conditions.

It is also possible to detect shocks, deflections and vibrations acting on the flexural resonator by using acceleration sensors in MEMS technology. For example, a pump running in the environment of the measuring device 4 could thus be detected on the basis of the vibration sensors 10 before the measurement. Therefore, even before the start of the measurement, a warning can be output that the measurement may be affected by errors. Measured values which chronologically accompany a shock or an impermissible deflection can be detected by the condition monitoring unit 2 and discarded. If necessary, an active system can also control out the oscillations.

Previously defined limiting values can also be matched to a desired accuracy class of the measurement and predefined.

It is also possible to use optical sensors, tribological sensors and so on for the measurement, for example for measuring the dust concentration in the environment of the measuring device 4 or else in the interior of the housing 20. In addition, the connection of flushing with clean and/or dry air for the housing 20 and/or the flexural resonator 12 and/or the dust sensor is automatically possible. In addition, automatic filtering of the interior of the housing via a filter and the supply of recirculated air at low positive pressure, for example circulation with a small pump through a filter and/or the supply of clean purging gas, are possible.

A sensor 6, 7, 8, 9, 10 for the monitoring of expected environmental parameters that are application-specific and impair the measurement can be connected in the environment of the housing 20 via an interface, and user-specific limiting values for these parameters can be integrated into the program of the condition monitoring unit 2 via an input unit.

During the measurement with the flexural resonator 12, the accuracy class of the measuring device 4 can then also be restricted on account of the measured environmental parameters, depending on the respectively input limiting values. The statement of non-meaningful decimal places for the density measurement can be suppressed by shortening and/or rounding; a warning can also be stored in addition to the output.

If, in the event of an output of a warning that the operating conditions are not safe, the measurement is nevertheless carried out, the state and the parameters are stored and, if appropriate, the device guarantee is nullified or the performance of the trial is permitted and the flexural resonator 12 is brought to a valid temperature by the condition monitoring unit 2, e.g. via a temperature control unit. This can also be carried out without any particular requirement for measurement with appropriate development of the environmental conditions. For instance, a high vapor concentration in the environment can lead automatically to heating of the flexural resonator 12 by the temperature control unit, in order to ensure safe conditions even in "stand-by".

When using a nonvolatile memory which stores incorrect operating conditions and provides the same for the maintenance and/or guarantee, the user can be requested to check or maintain the device in the event of frequent infringement of the permitted operating conditions.

The displays are carried out, irrespective of the respective measuring principle, by additional sensors; the software for this is adapted to the respective area of use.

The condition monitoring unit 2 can also function as a computing unit which can perform all the calculations, read data carriers according to the invention and/or in any case store measured values and parameters.

According to the invention, the influence of the ambient temperature on the measured result can be determined. If a series of measurements is started, the ambient temperature can be logged at the same time as each individual measured value and, on the basis of the known influence and the temperature change, the uncertainty on account of this effect can be indicated at the end of the series of measurements.

If the history of the ambient temperature is recorded, it is possible to predict with a certain probability how unreliable the measured result of a series of measurements will be. By means of the determination of the deviation of the ambient temperature from the ambient temperature during the adjustment, the expected uncertainty can be predicted on the basis of this influence.

This effect must not be disregarded, in particular during highly precise measurements.

In the case of non-encapsulated resonator variants, continuous operation with cold liquids below the dew point leads to the moist air condensing on the resonator pipe, which results in distortion of the measured result. This dependency can be determined for the device class in a series of tests. During operation, on the basis of the calculation of the dew point via the ambient temperature, the air pressure and the atmospheric humidity, the dew point can be determined. By using the measurement of the sample temperature and the duration of the filling, it is possible to determine by computation whether the measurement is valid, and ideally to determine the expected uncertainty.

By activating self-monitoring in thermostatic measuring devices, following a series of measurements that have been carried out below the dew point, the measuring device can be changed automatically into the safe temperature range again or, by brief heating of the measuring cell, the latter can be dried.

The environmental parameters are determined in the immediate surroundings of the flexural resonator and/or the measuring device and/or within the measuring device and/or within the housing of the flexural resonator.

The invention claimed is:

1. A method for determining a density of liquids, which comprises the steps of:
    providing a measuring device having a flexural resonator, the flexural resonator is accommodated in a housing of the measuring device, the measuring device further having at least one sensor for measuring at least one environmental parameter of the flexural resonator and of the measuring device that influences a measurement to be performed, the measuring device further having a condition monitoring unit;
    feeding measured values from the sensor to the condition monitoring unit, the condition monitoring unit having a memory unit with stored forecasts and prediction algorithms for environmental parameters to be expected in a course of a measurement and for operating states to be expected, and by using the condition monitoring unit, on a basis of the stored forecasts and the prediction algorithms and depending on at least one of present values or expected values of the environmental parameters and initial measured values or conditions selected for the measurement, it is determined whether the measurement can be carried out under at least one of selected trial conditions or initial values present at a start of measurement and/or with parameter values selected or expected in the course of the measurement, without any impairment or with a permissible impairment by expected or forecast changes in the environmental parameters; and
    wherein by using the condition monitoring unit, the measuring device is checked for safe conditions meeting a standard in an interior of the measuring device and in an environment of the housing for the flexural resonator including the housing being in an open state.

2. The method according to claim 1, wherein:
    the measuring device has at least one actuator for setting or controlling at least one environmental parameter; and
    the actuator before and/or during the measurement, controlling or setting at least one environmental parameter, on a basis of correction values which are determined by the condition monitoring unit or are predefined.

3. The method according to claim 1, wherein:
    when specific temperature values are reached or as early as when a temperature is predefined, a relative atmospheric humidity is pre-determined on a basis of atmospheric or environmental parameters present in an interior of the measuring device or an interior of a measuring cell of the housing of the flexural resonator, and conditions occurring are pre-determined even before a start of a required cooling; and/or
    monitoring and a prior calculation of a dew point are performed on a basis of a predefined, stored temperature profile and the environmental parameters present.

4. The method according to claim 1, which further comprises performing at least one of:
    outputting a warning via the condition monitoring unit when selected trial conditions are not safe or do not permit a correct measurement; or
    predefining a definition of limiting values for specific accuracy classes for exceeding permissible parameters.

5. The method according to claim 1, wherein:
    the measurement is one in a series of measurements to be performed; and
    the measurement measures at least one of atmospheric humidity, air pressure or air temperature.

6. A non-transitory computer reading medium comprising computer executable instructions for carrying out a method according to claim 1.

7. A measuring device for determining a density of liquids, comprising:
    a housing;
    a flexural resonator accommodated by said housing;
    at least one sensor for sensing at least one environmental parameter of said flexural resonator and of the measuring device that influences a measurement to be performed;
    a condition monitoring unit receiving measured values from said sensor, said condition monitoring unit having a memory unit with stored forecasts and prediction algorithms for determining values of environmental parameters to be expected in a course of a measurement and, on a basis of the stored forecasts and the prediction algorithms and depending on at least one of present values or predefined values of the environmental parameters and initial values of the environmental parameters selected for the measurement, it is determined whether a planned measurement can be carried out under selected trial conditions and/or with selected initial values and/or with parameter values selected or expected in the course of the measurement, without any impairment or with a permissible impairment by expected or forecast changes in the environmental parameters; and
    said condition monitoring unit checking whether the measuring device is operating under safe conditions that meet a standard for an interior of the measuring device and for an environment of said housing for said flexural resonator including said housing being in an open state.

8. The measuring device according to claim 7, further comprising at least one actuator for setting or controlling at least one environmental parameter, and with said actuator, before and/or during the measurement, at least one environmental parameter can be controlled or set, on a basis of correction values which are determined by said condition monitoring unit or are predefined.

9. The measuring device according to claim 8, wherein said actuator can be controlled or set by said condition monitoring unit.

10. The measuring device according to claim 8, wherein said actuator is one of a plurality of the actuators for setting at least one of a temperature, an air pressure, humidity, air composition or atmospheric dust content for the measuring device and/or for a close environment of the measuring device and/or for a surrounding area of said flexural resonator.

11. The measuring device according to claim 7, wherein said condition monitoring unit contains said sensor and said sensor is selected from the group consisting of a temperature sensor, a humidity sensor, an air pressure sensor, a dust concentration sensor, a vibration sensor and a shock sensor.

12. The measuring device according to claim 7, wherein said sensor performs a series of measurements and measures at least one of atmospheric humidity, air pressure or air temperature.

\* \* \* \* \*